United States Patent [19]

Lin et al.

[11] Patent Number: 4,978,655
[45] Date of Patent: Dec. 18, 1990

[54] USE OF 3′-DEOXYTHYMIDIN-2′-ENE (3′DEOXY-2′,3′-DIDEHYDROTHYMIDINE) IN TREATING PATIENTS INFECTED WITH RETROVIRUSES

[75] Inventors: Tai-Shun Lin, North Haven; William H. Prusoff, North Branford, both of Conn.

[73] Assignee: Yale University, New Haven, Conn.

[21] Appl. No.: 942,666

[22] Filed: Dec. 17, 1986

[51] Int. Cl.$^5$ .............................................. A61K 31/70
[52] U.S. Cl. ...................................... 514/50; 514/934
[58] Field of Search ................ 536/23; 514/49; 574/50

[56] References Cited

U.S. PATENT DOCUMENTS

| | | | |
|---|---|---|---|
| 3,322,747 | 5/1967 | Shen et al. | 536/23 |
| 3,817,982 | 6/1974 | Verheyden et al. | 536/23 |
| 4,360,522 | 11/1982 | Shaeffer et al. | 514/263 |
| 4,710,492 | 12/1987 | Lin et al. | 536/23 |

FOREIGN PATENT DOCUMENTS

| | | | |
|---|---|---|---|
| 0027783 | 3/1977 | Japan | 514/50 |
| 2027782 | 3/1977 | Japan | 536/23 |
| 254552 | 10/1986 | Japan | |
| 8700089 | 8/1988 | Netherlands | |

OTHER PUBLICATIONS

Mitsuya et al., Proc. Natl. Acad. Sci. USA, 82 pp. 7096-7100 (1985).
Mitsuya et al., Proc. Natl. Acad. Sci. USA, 83 pp. 1911-1915 (1986).
Fischl et al., The New England J. of Medicine, 317 No. 4, pp. 185-191 (1987).
Herdewijn et al., J. Med. Chem., 30 pp. 1270-1278 (1987).
Lin et al., Biochemical Pharmacolog, vol. 36, No. 17, pp. 2713-2718 (1987).
Lin et al., J. Med. Chem., 30 pp. 440-444 (1987).
Kim et al., J. Med. Chem., 30 862-866 (1987).
Lin et al., Biochemical Pharmacology, 36, No. 3, 311-316 (1987).
DeClercq, J. Antimicrobial Agents and Chemotherapy 14, Suppl. A, 85-95 (1984).
De Clercq et al., Biochemical Pharmacology, 29, 1849-1851 (1980).
Machida, Antimicrobial Agents and Chemotherapy, 29, No. 3, 524-526 (1986).
De Clercq, et al., J. Med. Chem., 29 213-217 (1986).
Robins, "Synthetic Antiviral Agents", (4 EN, Jan. 27, 1986.
D. Dormant, B. Spire, F. Barre-Sinoussi, L. Montagnier and J. C. Chermann, Ann. Inst. Pasteur/Virol., 75, 136E, (1985).
W. Rosenbaum, D. Dormont, B. Spire, E. Vilmer, M. Gentilini, C. Griscelli, L. Montagnier, F. Barre-Sinoussi and J. C. Chermann, Lancet, i, 450, (1985).
D. D. Ho, K. L. Hartshorn, T. R. Rota, C. A. Andrews, J. C. Kaplan, R. T. Schoolkey and M. S. Hirsch, Lancet, i, 602 (1985).
J. B. McCormick, J. P. Getchell, S. W. Mitchell and D. R. Hicks, Lancet, ii, 1367, (1984).
E. G. Sandstrom, J. C. Kaplan, R. E. Byington and M. S. Hirsch, Lancet, i, 1480, (1984).
P. S. Sarin, Y. Taguchi, D. Sun, A. Thornton, R. C. Gallo and B. Oberg, Biochem. Pharmac., 34, 4075, (1985).
R. Anand, J. L. Moore, A. Srinivason, V. Kalyanaraman, D. Francis, P. Feorino and J. Curran, Abstracts of the International Conference on Acquired Immune Deficiency Syndrome (AIDS), Apr. 14-17, Atlanta, Ga. p. 72, (1985).
H. Mitsuya, M. Popovic, R. Yarchoan, S. Matsushita, R. C. Gallo and S. Broder, Science, 226, 172, (1984).
H. Mitsuya, S. Matsushita, M. E. Harper and S. Broder, Cancer Res., 45, 4583s, (1985).
E. DeClercq, Cancer Lett. 8, 9 (1979).
A. Pompidou, D. Zagury, R. C. Gallo, D. Sun, A. Thornton and P. S. Sarin, Lancet, ii, 1423, (1985).
P. Chandra and P. S. Sarin, Drug Res., 36 184, (1986).
R. Anand, J. Moore, P. Feorino, J. Curran and A. Srinivasan, Lancet, i, 97, (1986).
P. S. Sarin, R. C. Gallo, D. I. Scheer, F. Crews and A. S. Lippa, New Engl. J. Med., 313, 1289, (1985).
W. Ostertag, T. Cole, T. Crozier, G. Gaedicke, J. Kind, N. Kluge, J. C. Krieg, G. Roselser, G. Sheinheider, B. J. Weimann and S. K. Dube, Proceedings of the 4th International Symposium of the Princess Takamatsu Cancer Research Fund, Tokyo, 1973, Differentiation and Control of Malignancy of Tumor Cells, Eds. W. Nakhara, T. Ono, T. Sugimura and H. Sugano, p. 485, University of Tokyo Press, Tokyo, (1974).
W. Ostertag, C. Roseler, C. J. Kreig, T. Cole, T. Crozier, G. Gaedicke, G. Steinheider, N. Kluge and S. K. Dube, Proc. Natn. Acad. Sci. USA, 71, 4980, (1974).
S. L. Dube, G. Gaedicke, N. Kluge, B. J. Weimann, H. Melderis, G. Steinheider, T. Crozier, H. Beckmann and W. Ostertag, Proceedings of the 4th International Symposium of the Princess Takamatsu Cancer Research Fund, Tokyo, 1973, Differentiation and Control of Malignancy of Tumor Cells, Eds. W. Nakahara, T. Ono, T. Sugimura and H. Sugano, p. 99, University of Tokyo Press, Tokyo, (1974).
S. K. Dube, I. B. Pragnell, N. Kluge, G. Gaedicke, G. Steinheider and W. Ostertag, Proc. Natn. Acad. Sci., USA, 72, 1863, (1975).
H. Mitsuya, K. J. Weinhold, P. A. Furman, M. H. St. Clair, S. Lehrman Nusinoff, R. C. Gallo, D. Bolognesi,
(List continued on next page.)

Primary Examiner—John W. Rollins
Attorney, Agent, or Firm—Sprung Horn Kramer & Woods

[57] ABSTRACT

This invention relates to the use of 3′-deoxythymidin-2′-ene (3′deoxy-2′,3′-didehydrothymidine) in treating patients infected with a retrovirus.

8 Claims, No Drawings

OTHER PUBLICATIONS

D. W. Barry and S. Broder, *Proc. Natn. Acad. Sci.* USA, 82, 7096, (1985).

H. Mitsuya and S. Broder, *Proc. Natn. Acad. Sci. USA*, 83, 1911, (1986).

E. DeClerq, *J. Med. Chem.*, 29, 1561, (1986).

Lin et al., *Biochem. Pharmacol*, in press.

J. P. Horwitz, J. Chua, M. A. Da Rooge, M. Noel and I. L. Klundt, *J. Org. Chem.* 31, 205 (1986).

European Search Report.

Biochemical and Biophysical Research Communications, pp. 128–134, vol. 142, No. 1, 1987, Jan. 15, 1987.

The Anti-Htlv-111(Anti-HIV)and Cytotoxic Activity of 2'3'-Didehydro-2'3'-dideoxyribonucleosides: A comparison with their Parental 2',3'-Dideoxyribonucleosides Jan Balzarini et al., Mol. Pharmacol. 32 (1) Jul. 1981, pp. 162–167.

Inhibition by 2', 3'-Dideoxythymidine or Retroviral Infection of Mouse and Human Cells, Philip Furmanski et al., Cancer Letters 8 (1980) pp. 307–315.

Potent and Selective Anti-HTLV-III/Lav Activity of 2', 3', Dideoxycytidinene, The 2', 3'-Unsaturated Derivative of 2', 3'-Dideoxycytidine, Jan Balzarini et al., Biochem. Bioplays. Res. Commun. pp. 735–742, vol. 140, No. 2, 1986.

Inhibition of the in vitro infectivity and cytopathic effect of human T-lymphotrophic virus type III/lymphadenopathy-associated virus (HTLV-III/LAV) by 2', 3'-dideoxynucleosides; Hiroadki Mitsuya et al., vol. 83, pp. 1911-1915, Mar. 1986, Proc. Natl. Acad. Sci. U.S.A.

Synthesis of Uracil and Thymine Nucleosides of Unsaturated 5-(Aminoacyl) Aminopentofuranoses, Takeshi Adachi et al., pp. 113–124, Carbohydrate Research, 73 (1979).

Derwent abstract No. 88-170966/25.

USE OF 3'-DEOXYTHYMIDIN-2'-ENE (3'DEOXY-2',3'-DIDEHYDROTHYMIDINE) IN TREATING PATIENTS INFECTED WITH RETROVIRUSES

GOVERNMENT RIGHTS

This invention was made with United States government support under Grant CA-28852 from the NIH. The United States Government has certain rights in this invention.

BACKGROUND OF THE INVENTION

1. Field of the Invention

The present invention concerns the use of 3'-deoxythymidin-2'-ene (3'-deoxy-2', 3 -didehydrothymidine) in treating patients infected with retroviruses.

2. Background Information

Acquired immunodeficiency syndrome (AIDS) is generally accepted to be a consequence of infection with the retrovirus variously termed human T-lymphotropic virus type III (HTLV-III), lymphadenopathy-associated virus (LAV), AIDS associated retrovirus (ARV), or human immunodeficiency virus (HIV). A number of compounds have demonstrated antiviral activity against this virus which include HPA-23 (D. Dormont, B. Spire, F. Barre-Sinoussi, L. Montagnier and J. C. Chermann, *Ann. Inst. Pasteur/Virol.*, 75, 136E, (1985) and W. Rosenbaum, D. Dormont, B. Spire, E. Vilmer, M. Gentilini, C. Griscelli, L. Montagnier, F. Barre-Sinoussi and J. C. Chermann, *Lancet* i, 450, (1985)), interferons (D. D. Ho, K. L. Hartshorn, T. R. Rota, C. A. Andrews, J. C. Kaplan, R. T. Schoolkey and M. S. Hirsch, *Lancet*, i, 602, (1985)), , ribavirin (J. B. McCormick, J. P. Getchell, S. W. Mitchell and D. R. Hicks, *Lancet*, ii, 1367, (1984)), phosphonoformate (E. G. Sandstrom, J. C. Kaplan, R. E. Byington and M. S. Hirsch, *Lancet*, i 1480 (1984) and P. S. Sarin, Y. Taguchi, D. Sun, A. Thornton, R. C. Gallo and B. Oberg, *Biochem. Pharmac.*, 34, 4075, (1985)), ansamycin (R. Anand, J. L. Moore, A. Srinivason, V. Kalyanaraman, D. Francis, P. Feorino and J. Curran, *Abstracts of the International Conference on Acquired Immune Deficiency Syndrome (AIDS)*, April 14–17, Atlanta, GA, page 72, (1985)), suramin (H. Mitsuya, M. Popovic, R. Yarchoan, S. Matsushita, R. C. Gallo and S. Broder, *Science*, 226, 172, (1984); H. Mitsuya, S. Matsushita, M. E. Harper and S. Broder, *Cancer Res.*, 45, 4583s, (1985) and E. DeClercq, *Cancer Lett.*, 8, 9, (1979)), imuthiol (A. Pompidou, D. Zagury, R. C. Gallo, D. Sun. A. Thornton and P. S. Sarin, *Lancet*, ii, 1423, (1985)), penicillamine (P. Chandra and P. S. Sarin, *Drug Res.*, 36, 184, (1986)), rifabutin (R. Anand, J. Moore, P. Feorino, J. Curran and A Srinivasan, *Lancet*, i, 97, (1986)), AL-721 (P. S. Sarin, R. C. Gallo, D. I. Scheer, F. Crews and A. S. Lippa, *New Engl. J. Med.*, 313, 1289, (1985)), 3'-azido-3'deoxythymidine (W. Ostertag T. Cole, T. Crozier, G. Gaedicke, J. Kind, N. Kluge, J. C. Krieg. G. Roselser, G. Sheinheider, B. J. Weimann and S. K. Dube, *Proceedings of the 4th International Symposium of the Princess Takamatsu Cancer Research Fund*, Tokyo, 1973, *Differentiation and Control of Malignancy of Tumor Cells*, Eds. W. Nakahara, T. Ono, T. Sugimura and H. Sugano, page 485, University of Tokyo Press, Tokyo, (1974); W. Ostertag, G. Roseler, C. J. Kreig, T. Cole, T. Crozier, G. Gaedicke, G. Steinheider, N. Kluge and S. K. Dube, *Proc. Natn. Acad. Sci. USA*, 71, 4980, (1974); S. L. Dube, G. Gaedicke, N Kluge, B. J. Weimann, H. Melderis, G. Steinheider T. Crozier, H. Beckmann and W. Ostertag, *Proceedings of the 4th International Symposium of the Princess Takamatsu Cancer Research Fund*, Tokyo, 1973, *Differentiation and Control of Malignancy of Tumor Cells*, Eds. W. Nakahara. T. Ono, T. Sugimura and H. Sugano, page 99, University of Tokyo Press, Tokyo, (1974); S. K. Dube, I. B. Pragnell, N. Kluge, G. Gacdicke, G. Steinheider and W. Ostertag, *Proc. Natn. Acad. Sci. USA*, 72, 1863, (1975) and H. Mitsuya, K. J. Weinhold, P. A. Furman, M. H. St. Clair, S. Lehrman Nusinoff, R. C. Gallo, D. Bolognesi, D. W. Barry and S. Broder, *Proc. Natn. Acad. Sci. USA*, 82, 7096, (1985)), and more recently various 2', 3'-dideoxynucleosides (H. Mitsuya and S. Broder, *Proc. Natn. Acad. Sci. USA*, 83, 1911, (1986)), of which 2',3'-dideoxycytidine (ddCyd) is the most potent. A review of these and other compounds evaluated for their activities against HIV, as well as a discussion of the AIDS problem in general, has been presented (E. DeClercq, *J. Med. Chem.*, 29, 1561, (1986)).

Applicants previously found 2', 3'-dideoxycytidin-2'-ene (2', 3'-dideoxy-2', 3'-didehydrocytidine; D4C) a derivative of 2', 3'-dideoxycytidine (ddCyd) to have antiviral activity against HIV (Lin et al, *Biochem. Pharmacol*, in press). This provided the stimulus to synthesis 3'-deoxythymidin-2'-ene (3'-deoxy-2', 3'-didehydrothymidine) even though Mitsuya and Broder, supra found 2', 3'-dideoxythymidine (3'-deoxythymidine) to be a very poor inhibitor of HTLV-III/LAV. Applicants' finding of potent antiviral activity with 3'-deoxythymidin-2'-ene was, therefore, unexpected based on their report.

SUMMARY OF THE INVENTION

The present invention is directed to the treatment of warm blooded animals, including humans, infected with a retrovirus comprising administering to a warm blood animal, e.g., a human patient, an anti-retroviral effective amount of 3'-deoxythymidin-2'-ene (3'-deoxy-2', 3'-didehydrothymidine), either alone or in admixture with a diluent or in the form of a medicament.

DETAILED DESCRIPTION OF THE INVENTION

The structure of 3'-deoxythymidin-2'-ene (3'-deoxy-2', 3'-didehydrothymidine; D4T) is as follows:

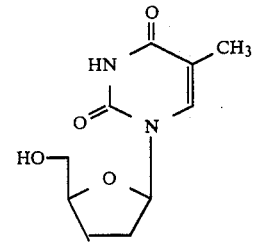

3'-Deoxythymidin-2'-ene (3'-deoxy-2', 3'-didehydrothymidine) has antiviral activity against retroviruses, e.g., murine leukemia virus and human immunodeficiency virus, i.e., HIV; HTLV III/LAV virus (the AIDS virus).

Retroviruses are RNA viruses whose genome contains copies of high-molecular weight single-stranded RNA. The virion contains reverse transcriptase. Non-limiting examples of retroviruses include leukemia and sarcoma viruses of animals, foamy viruses of primates and some slow viruses, e.g., visna and maedi of sheep.

A synthesis for the active compound of the present invention is illustrated in the following reaction scheme:

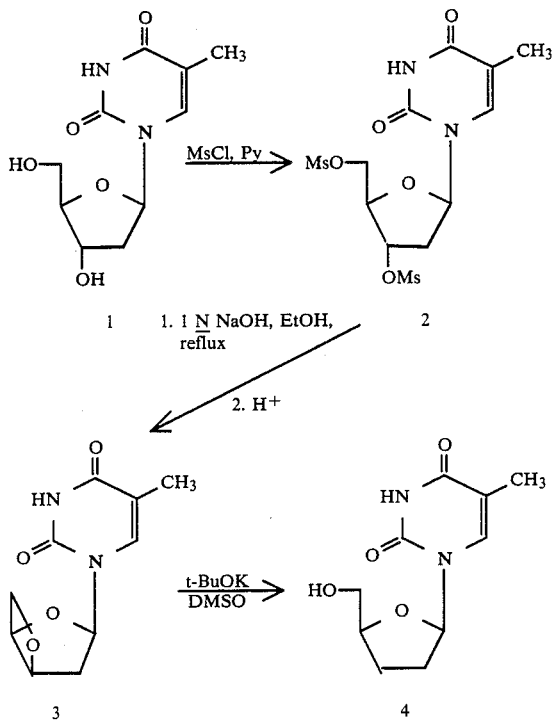

3,-Deoxythymidin-2-,ene (3,-deoxy-2',3,-didehydrothymidine) (4) can be synthesized basically by the methodology of J. P. Horwitz, J. Chua, M. A. DaRooge, M. Noel and I. L. Klundt, *J Org. Chem.*, 31, 205, (1966) with minor modifications. With reference to the above reaction scheme, treatment of thymidine (1) with methanesulfonyl chloride in pyridine at 0° C. gives the corresponding disulfonate 2. Refluxing compound,, 2 with 1 N NaOH solution in ethanol produces the 3',5'-cyclic ether 3. Treatment of compound 3 with potassium t-butoxide in dry DMSO yields the desired 2', 3'-unsaturated derivative 4.

The present invention provides a pharmaceutical composition containing as an active ingredient 3'-deoxythymidin-2'-ene (3'-deoxy-2', 3'-didehydrothyn'idine) in admixture with a solid, liquid or liquefied gaseous diluent.

The invention further provides a pharmaceutical composition containing as an active ingredient the 3'-deoxythumidin-2'-ene (3'-deoxy-2', 3'-didehydrothymidine) in the form of a sterile and/or physiologically isotonic aqueous solution The invention also provides a medicament in dosage unit form comprising 3'-deoxythymidin-2'-ene (3'-deoxy-2', 3'-didehydrothymidine).

The invention also provides a medicament in the form of tablets (including lozenges and granules), caplets, dragees, capsules, pills, ampoules or suppositories comprising 3'-deoxythymidin-2'-ene (3'-deoxy-2', 3'-didehydrothymidine).

"Medicament" as used herein means physically discrete coherent portions suitable for medical administration. "Medicament in dosage unit form" as used herein means physically discrete coherent units suitable for medical administration, each containing a daily dose or a multiple (up to four times) or a sub-multiple (down to a fortieth) of a daily dose of the compound of the invention in association with a carrier and/or enclosed within an envelope. Whether the medicament contains a daily dose, or for example, a half, a third or a quarter of a daily dose will depend on whether the medicament is to be administered once or, for example, twice, three times or four times a day, respectively.

The pharmaceutical compositions according to the invention may, for example, take the form of suspensions, solutions and emulsions of the active ingredient in aqueous or non-aqueous diluents, syrups, granulates or powders.

The diluents to be used in pharmaceutical compositions (e.g., granulates) adapted to be formed into tablets, dragees, capsules and pills include the following: (a) fillers and extenders, e.g., starch, sugars, mannitol and silicic acid; (b) binding agents, e.g., carboxymethyl cellulose and other cellulose derivatives, alginates, gelatine and polyvinyl pyrrolidone; (c) moisturizing agents, e.g., glycerol; (d) disintegrating agents, e.g., agaragar, calcium carbonate and sodium bicarbonate; (e) agents for retarding dissolution, e.g., paraffin; (f) resorption accelerators, e.g, quaternary ammonium compounds; (g) surface active agents, e.g., cetyl alcohol, glycerol monostearate; (h) adsorptive carriers, e.g., kaolin and bentonite; (i) lubricants, e.g., talc, calcium and magnesium stearate and solid polyethyl glycols.

The tablets, dragees, capsules, caplets and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, from polymeric substances or waxes.

The active ingredient can also be made up in microencapsulated form together, with one or several of the above-mentioned diluents.

The diluents to be used in pharmaceutical compositions adapted to be formed into suppositories can, for example, be tho usual water-soluble diluents, such as polyethylene glycols and fats (e.g., cocoa oil and high esters, [e.g., $C_{14}$-alcohol with $C_{16}$-fatty acid]) or mixtures of these diluents.

The pharmaceutical compositions which are solutions and emulsions can, for example, contain the customary diluents (with, of course, the above-mentioned exclusion of solvents having a molecular weight below 200, except in the presence of a surface-active agent), such as solvents, dissolving agents and emulsifiers. Specific non-limiting examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils (for example, ground nut oil), glycerol, tetrahydrofurfuryl alcohol, polyethylene glycols and fatty acid esters of sorbitol or mixtures thereof.

For parenteral administration, solutions and emulsions should be sterile and, if appropriate, blood-isotonic.

The pharmaceutical compositions which are suspensions can contain the usual diluents, such as liquid diluents, e.g., water, ethyl alcohol, propylene glycol, surface-active agents (e.g., ethoxylated isostearyl alcohols, polyoxyethylene sorbite and sorbitane esters), microcrystalline cellulose, aluminium metahydroxide, bentonite, agar-agar and tragacanth or mixtures thereof.

All the pharmaceutical compositions according to the invention can also contain coloring agents and preservatives, as well as perfumes and flavoring additions (e.g., peppermint oil and eucalyptus oil) and sweetening agents (e.g., saccharin and aspartame).

The pharmaceutical compositions according to the invention generally contain from 0.5 to 90% of the active ingredient (3'-deoxythymidin-2'-ene (3'-deoxy-2',3'-didehydrothymidine)) by weight of the total composition.

In addition to 3'-deoxythymidin-2'-ene (3'-deoxy-2',3'-didehydrothymidine), the pharmaceutical compositions and medicaments according to the invention can also contain other pharmaceutically active compounds.

Any diluent in the medicaments of the present invention may be any of those mentioned above in relation to the pharmaceutical compositions of the present invention. Such medicaments may include solvents of molecular weight less than 200 as the sole diluent.

The discrete coherent portions constituting the medicament according to the invention will generally be adapted by virtue of their shape or packaging for medical administration and may be, for example, any of the following: tablets (including lozenges and granulates), pills, dragees, capsules, suppositories and ampoules. Some of these forms may be made up for delayed release of the active ingredient. Some, such as capsules, may include a protective envelope which renders the portions of the medicament physically discrete and coherent.

The preferred daily dose for administration of the medicaments of the invention is 2.5 to 250 mg of active ingredient in the case of intravenous administration and 25 to 250 mg of active ingredient in the case of oral administration.

The production of the above-mentioned pharmaceutical compositions and medicaments is carried out by any method known in the art, for example, by mixing the active ingredient(s) with the diluent(,s) to form a pharmaceutical composition (e.g., a granulate) and then forming the composition into the medicament (e.g. tablets).

This invention provides a method for treating the above-mentioned diseases in warm-blooded animals, which comprises administering to the animals the compound of the invention, namely, 3'-deoxythymidin-2'-ene (3'-deoxy-2', 3'-didehydrothymidine), alone or in admixture with a diluent or in the form of a medicament according to the invention.

It is envisaged that this active compound, namely, 3'-deoxythymidin-2'-ene (3'deoxy-2', 3'-didehydrothymidine), will be administered perorally, parenterally (for example, intramuscularly, intraperitoneally, subcutaneously or intravenously), rectally or locally, preferably orally or parenterally, especially perlingually or intravenously. Preferred pharmaceutical compositions and medicaments are, therefore, those adapted for administration such as oral or parenteral administration. Administration in the method of the invention is preferably oral or parenteral administration.

In general, it has proved advantageous to administer intravenously amounts of from 0.01 mg to 10 mg/kg, preferably 0.05 to 5 mg/kg, of body weight per day and to administer orally 0.05 to 20 mg/kg, preferably 0.5 mg to 5 mg/kg of body weight per day, to achieve effective results. Nevertheless, it can at times be necessary to deviate from those dosage rates, and in particular to do so as a function of the nature and body weight of the human or animal subject to be treated, the individual reaction of this subject to the treatment, type of formulation in which the active ingredient is administered, the mode in which the administration is carried out and the point in the progress of the disease or interval at which it is to be administered. Thus, it may in some case suffice to use less than the above-mentioned minimum dosage rate, whilst other cases the upper limit mentioned must be exceeded to achieve the desired results. Where larger amounts are administered, it may be advisable to divide these into several individual administrations over the course of the day.

The invention will now be described with reference to the following non-limiting examples.

EXAMPLE 1:

SYNTHESIS OF 3'-DEOXYTHYMIDIN-2'-ENE (3'-DEOXY-2', 3 -DIDEHYDROTHYMIDINE)

A solution of the cyclic ether 3 (see the reaction scheme described hereinabove) (8.64 g, 38.4 mmol) in 240 ml of dried DMSO containing 8.70 g (76.4 mmol) of potassium t-butoxide was stirred at room temperature for two hours. The reaction mixture was neutralized to a pH of approximately 7 with ethanolic acetic acid, and the solution was then evaporated to dryness at approximately 50° C. under reduced pressure. The residue was triturated with several portions of hot acetone. The insoluble materials were removed by filtration, and the filtrate was evaporated to dryness. The residue was eluted through a silica gel column (CHCl$_3$-EtOH, 2:1) to yield 6.5 g (76%) of product: mp 158°–160° C.; (Me$_2$-SO-d$_6$) $\delta$1.82 (s, 3H, 5-CH$_3$), 3.53 (m, 2H, 5'-H), 4.80 (m, 1H, 4'-H), 4.96 (t, 1H, 5'-OH, D$_2$O exchangeable), 5.90 (m, 1H, 3'-H, vinyl), 6.40 (m, 1H, 2'-H, vinyl), 6.82 (m, 1H, 1'-H), 7.67 (s, 1H, 6-H).

EXAMPLE 2:

BIOLOGICAL ASSAY PROCEDURE FOR ANTIVIRAL ACTIVITY AGAINST THE HUMAN IMMUNODEFICIENCY VIRUS (HIV; HTLV-III/LAV)

Three day-old mitogen stimulated human peripheral blood mononuclear (PBM) cells (10$^6$ per ml) were infected with HIV (strain LAV) in the presence and absence of various concentrations of 3-deoxythymidin-2'-ene, 1, 10, 100 $\mu$M. Five days after infection, the virus in the supernatant was pelleted and, after disruption, the reverse transcriptase activity was determined.

The methods used for culturing the PBM cells, harvesting the virus and determination of reverse transcriptase activity were those described by J. S. McDougal, S. P. Cort, M. S. Kennedy, C. D. Cabridilla, P. M. Feorino, D. P. Francis, D. Hicks, V. S. Kalyanaramen and L. S. Martin, *J. Immun. Meth.*, 76, 171, (1985). The virus was added to the cultures at the same time as the drug.

The data obtained indicated that essentially complete inhibition of the replication of the "AIDS" virus was obtained (>98% inhibition) at all three concentrations.

EXAMPLE 3:

BIOLOGICAL ASSAY PROCEDURE FOR ANTIVIRAL ACTIVITY AGAINST MOLONEY MURINE LEUKEMIA VIRUS (M-MuLV) BY XC-ASSAY

The XC assay system is an indirect method for quantitation of murine-leukemia virus (MuLV) originally described by V. Klement, W. P. Rowe, J. W. Hartley and W. E. Pugh, *Proc. Natl. Acad. Sci.*, 63, 753, (1969) and modified by W. P. Rowe, W. E. Pugh and J. W. Hartley, *Virology*, 42, 1136, (1970). This test is based on the development of syncytial changes in the XC cell line when it is co-cultivated with mouse fibroblast cells (SC-1 cells) productively infected with MuLV. The XC cell line was derived from a rat tumor induced by the prague strain of Rouse Sarcoma Virus (RSV) (J. Svoboda, P. Chyle, D. Simkovic and J. Hilgert, *Folia Biol.*, 9, 77, 1963)). This cell line contains the RSV genome, but does not produce infectious virus in the absence of a helper virus.

10E6 SC-1 cells were seeded in Earls Minimum Essential Medium (EMEM)-10% Fetal Bovine Serum (FBS), onto 60 mm petri dishes. The following day, the cells were inoculated with 0.5 ml of a virus dilution containing 25 µg/ml of DEAE-dextran. The dishes were maintained for 1 hour at 37° C. in a humidified 5% $CO_2$ incubator. The virus inoculum was then removed and replaced with 5 ml of medium containing appropriate concentrations of the test compound (two dishes/concentration). Medium containing 10% FBS was added to the virus control dishes. The medium (with or without the test compound) was changed at 48 hours.

Five days after virus inoculation, the culture fluid was decanted, and the cells were irradiated with a "General Electric" germicidal bulb for 30 seconds (1500-1800 ergs UV-light). Cultures were immediately overlaid with 10E6 SC cells in 5 ml of EMEM-10% FBS/dish. The medium was changed at 2-day intervals. Four days after XC cells addition, cultures were simultaneously fixed and stained with GEIMSA for 10 to 15 minutes.

Plaques were counted using an inverted microscopy as holes in the cell sheet containing syncytial cells, or as focal masses of multinucleated giant cells. The antiviral activity was highly significant and had an $ED_{50}$ of 2.5 µM.

Calculation of % Inhibition/Concentration (% Inh./conc.):

$$\% \text{ Inh./conc.} = 100 - \left[ \frac{\text{average \# of syncytial/conc. of test compound}}{\text{average \# of syncytia/in the virus control}} \times 100 \right]$$

$ED_{50}$: Accumulative % Inhibition using the Reed-Muench Method

It will be appreciated that the instant specification and claims are set forth by way of illustration and not limitation and that various modifications and changes may be made without departing from the spirit and scope of the present invention.

What is claimed is:

1. A method for treating warm blooded animals infected with a retrovirus, the method comprising administering to the warm blooded animal an anti-retroviral effective amount of 3'-deoxythymidin-2'-ene, either alone or in admixture with a diluent or in the form of a medicament.

2. A method according to claim 1, wherein the retrovirus is Moloney murine leukemia virus.

3. A method according to claim 1, wherein the retrovirus is HTLV III/LAV.

4. A method according to claim 1, wherein the 3'-deoxythymidine-2'-ene is administered intravenously in an amount of 0.01 to 10 mg per kg body weight per day.

5. A method according to claim 1 wherein the 3'-deoxythymidin-2'-ene is in admixture with a solid, liquid or liquified gaseous diluent to form a pharmaceutical composition.

6. A method according to claim 5, wherein the pharmaceutical composition contains 0.5 to 90% of said 3'-deoxythymidin-2'-ene.

7. A method according to claim 5, wherein the pharmaceutical composition is in the form of a sterile physiologically isotonic aqueous solution.

8. A method for treating human blood cells infected with HIV comprising administering to said cells an antiretroviral effective amount of 3'-deoxythymidin-2'-ene either alone or in admixture with a diluent or in the form of a medicament.

* * * * *

UNITED STATES PATENT AND TRADEMARK OFFICE
CERTIFICATE OF CORRECTION

PATENT NO.   : 4,978,655
DATED        : December 18, 1990
INVENTOR(S)  : Lin et al.

It is certified that error appears in the above-identified patent and that said Letters Patent is hereby corrected as shown below:

Title Page          [54] TITLE:  2nd line after 1st 3' " insert -- - --

Col. 1, line 2      Second line of Title after 1st " 3' " insert -- - --

Col. 2, lines 50-   Delete " 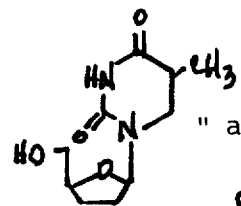 " and substitute -- 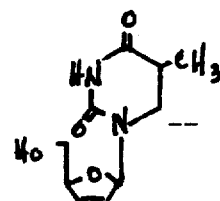 --

Col. 3, lines 23-   No. 4 delete " 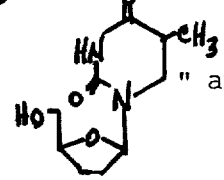 " and substitute -- 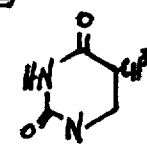  --

UNITED STATES PATENT AND TRADEMARK OFFICE
CERTIFICATE OF CORRECTION

PATENT NO. : 4,978,655
DATED : December 18, 1990
INVENTOR(S) : Lin, et al.

It is certified that error appears in the above-identified patent and that said Letters Patent is hereby corrected as shown below:

Col. 3, line 49    Delete " didehydrothynidine " and substitute
                   -- didehydrothymidine --

Signed and Sealed this

Twenty-seventh Day of October, 1992

*Attest:*

DOUGLAS B. COMER

*Attesting Officer*    *Acting Commissioner of Patents and Trademarks*

UNITED STATES PATENT AND TRADEMARK OFFICE

CERTIFICATE EXTENDING PATENT TERM
UNDER 35 U.S.C. § 156

PATENT NO.      : 4,978,655

DATED           : December 18, 1990

INVENTOR(S)     : Tai-Shun Lin et al.

PATENT OWNER    : Yale University

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of

189 DAYS with all rights pertaining thereto as provided by 35 U.S.C. § 156(b).

I have caused the seal of the Patent and Trademark Office to be affixed this 23rd day of January 1996.

Bruce A. Lehman
Assistant Secretary of Commerce and
   Commissioner of Patents and Trademarks